United States Patent
Kershman et al.

(10) Patent No.: US 12,396,935 B2
(45) Date of Patent: Aug. 26, 2025

(54) REDUCED ODOR FORMALDEHYDE-CONTAINING ANTISEPTIC LOTION

(71) Applicant: Shear Kershman Laboratories, Inc., Chesterfield, MO (US)

(72) Inventors: Alvin Kershman, St. Louis, MO (US); Jeff Shear, Bonita Springs, FL (US); Doreen Linze, Labadie, MO (US); Olaf Hansen, Dusseldorf (DE)

(73) Assignee: Shear Kershman Laboratories, Inc., Chesterfield, MO (US)

( * ) Notice: Subject to any disclaimer, the term of this patent is extended or adjusted under 35 U.S.C. 154(b) by 8 days.

(21) Appl. No.: 18/580,809

(22) PCT Filed: Jul. 26, 2022

(86) PCT No.: PCT/US2022/038293
§ 371 (c)(1),
(2) Date: Jan. 19, 2024

(87) PCT Pub. No.: WO2023/009486
PCT Pub. Date: Feb. 2, 2023

(65) Prior Publication Data
US 2025/0090434 A1    Mar. 20, 2025

Related U.S. Application Data

(60) Provisional application No. 63/226,510, filed on Jul. 28, 2021.

(51) Int. Cl.
A61K 8/33 (2006.01)
A61K 8/34 (2006.01)
A61K 8/92 (2006.01)
A61Q 17/00 (2006.01)

(52) U.S. Cl.
CPC ............ *A61K 8/33* (2013.01); *A61K 8/345* (2013.01); *A61K 8/92* (2013.01); *A61Q 17/005* (2013.01); *A61K 2800/30* (2013.01)

(58) Field of Classification Search
CPC ............ A61K 8/33; A61K 8/345; A61K 8/92; A61K 2800/30; A61Q 17/005
See application file for complete search history.

(56) References Cited

U.S. PATENT DOCUMENTS 6,383,505 B1 * 5/2002 Kaiser ............... A61K 31/14
424/407
8,586,102 B2  11/2013 Rocker et al.
9,173,941 B1  11/2015 Shear et al.

OTHER PUBLICATIONS

Supplementary European Search Report of EP Application No. 2285016 dated Jun. 26, 2025.
Database Medline, US National Library of Medicine, Bethesda, MD, May 24, 1986, Arkins S. et al., "Effects of formalin footbathing on foot disease and claw quality in dairy cows," XP002813602, pp. 580-583.

* cited by examiner

*Primary Examiner* — Jeffrey S Lundgren
*Assistant Examiner* — Ibrahim D Bori
(74) *Attorney, Agent, or Firm* — Dentons US LLP

(57) ABSTRACT

An alcohol-free lotion for the topical application having antiseptic properties is made by combining an aqueous phase comprising formaldehyde and at least one humectant with an oil phase comprising at least one surfactant and at least one oil; wherein the at least one humectant is present in the aqueous phase in the range of from 30 to 75 wt. %., wherein formaldehyde is present in the aqueous phase in the range of from about 1.0 to 20.0 wt. %; wherein the surfactant is present in the oil phase in the range of from about 30 to 60 wt. %; wherein the aqueous phase to oil phase ratio is from about 10:1 to 4:1; and wherein the lotion free of the odor of formaldehyde.

10 Claims, No Drawings

REDUCED ODOR FORMALDEHYDE-CONTAINING ANTISEPTIC LOTION

CROSS-REFERENCE TO RELATED APPLICATIONS

This application claims the benefit of provisional patent application 63/226,510 filed Jul. 28, 2021 which is hereby incorporated by reference.

STATEMENT REGARDING FEDERALLY SPONSORED RESEARCH

Not Applicable.

APPENDIX

Not Applicable.

FIELD OF THE INVENTION

The present invention relates to an antiseptic lotion, and more particularly to a hydrophobic antiseptic lotion containing formaldehyde which does not have a formaldehyde odor.

BACKGROUND OF THE INVENTION

Formaldehyde is a bactericidal solution that kills most bacteria, bacterial spore and viruses and is used as a reliable disinfectant and fumigant. It also destroys superficial tissue and has been used in footbaths for treatment of foot rot infections of hoof corium and claws. Formaldehyde is inexpensive and readily available solution with high consumption in dairy cow farms. Also, formaldehyde has been used frequently in combination with other components in dentistry.

The vapors of formaldehyde are very irritating and it is classified as a potential carcinogen. Care must be taken to protect users from the fumes when mixing and using formaldehyde solution, and to not dilute with chlorinated water as a dangerous gas can be produced. Users should wear gloves to avoid skin contact, protect eyes from splashes, limit exposure time and use these solutions only in a well ventilated area. Symptoms of toxic and side effects of formaldehyde in human are published frequently and attention to them is necessary.

It is desirable to have an antiseptic lotion that uses formaldehyde as an active, but does not emit the formaldehyde fumes. In 1973, Ralph Truhillo et. al published a study of the antiseptic effectiveness of formaldehyde solutions using different solvents. The solvents used with formaldehyde were water, glycerol, propylene glycol and ethylene glycol. The organic solutions were as effective as the aqueous solution as antiseptic agents, and the organic solutions did not emit the formaldehyde odor. Unlike the present invention, these organic solutions of formaldehyde are water soluble, and fail to provide a stable, hydrophobic lotion that did not readily wash off. Additionally, the ethylene glycol component is a toxic compound and is undesirable for this application.

U.S. Pat. Nos. 2,347,012, 2,519,565, 3,350,265, 4,022,911, 4,125,628, 9,220,799, and 9,750,755 provide examples of antiseptic compositions using formaldehyde, typically combined with other antiseptic actives, which are hereby incorporated by reference. Particularly, U.S. Pat. No. 8,586,102 discloses the use of non-formaldehyde antimicrobials, such as stannous fluoride and zinc sulfate, as well as copper sulfate, hydrogen peroxide and antibiotics, which are all not suitable for the present invention, as all of these antimicrobials have toxic and/or adverse environmental properties. Additionally, hydrogen peroxide destabilizes the claimed antiseptic lotion.

SUMMARY OF THE INVENTION

The present invention is a homogeneous topical lotion wherein the lotion contains from about 2.0 to 15 wt. % at least one surfactant, from about 2.0 to 15.0 wt. % at least one oil, from about 25.0 to 75.0 wt. % at least one humectant, from about 10 to 50 wt. % water, and from about 0.1 to 12.0 wt. % formaldehyde. The lotion does not contain non-formaldehyde antimicrobials that have toxic and/or adverse environmental properties. The lotion does not have a formaldehyde odor.

The present invention is made by combining an aqueous phase comprising water, at least one humectant and formaldehyde with an oil phase comprising at least one surfactant and at least one oil to form a topical lotion with hydrophobic properties. The at least one humectant is present in the aqueous phase in the range of from about 30.0 to about 75.0 wt. %. In a preferred embodiment, the at least one humectant is present in the aqueous phase from about 40.0 to 75.0 wt. %. The aqueous phase contains formaldehyde in the range of about 1.0 to 20.0 wt. %. The surfactant is present in the oil phase in the range of from about 30.0 to 60.0 wt. %. In a preferred embodiment, the surfactant is present in the oil phase from about 40 to 60 wt. %. The aqueous phase is added to the oil phase in a weight ratio of about 10:1 to 4:1. The aqueous phase is added to the oil phase using low to medium shear mixing to provide the homogeneous hydrophobic topical lotion. The lotion is stable, hydrophobic, and has antiviral properties.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses.

The present invention is a homogeneous topical lotion wherein the lotion contains from about 2.0 to 15 wt. % surfactant, from about 2.0 to 15.0 wt. % oil, from about 25.0 to 75.0 wt. % humectant, from about 10 to 50 wt. % water, from about 0.1 to 12.0 wt. % formaldehyde. The present invention is made by combining an aqueous phase comprising formaldehyde, water and at least one humectant with an oil phase to form a topical lotion with hydrophobic properties. The at least one humectant is present in the aqueous phase in the range of from about 25.0 to about 75.0 wt. %. In a preferred embodiment, the at least one humectant is present in the aqueous phase from about 30.0 to 75.0 wt. %. The oil phase comprises at least one surfactant and at least one oil. The surfactant is present in the oil phase in the range of from about 30 to 60 wt. %. In a preferred embodiment, the surfactant is present in the oil phase from about 40 to 60 wt. %. The aqueous phase is added to the oil phase in a weight ratio of about 10:1 to 4:1. The aqueous phase is added to the oil phase using low to medium shear mixing to provide the homogeneous hydrophobic topical lotion. The lotion is stable, hydrophobic, and has antimicrobial properties.

The oil phase is prepared from a hydrophobic solution or mixture containing optionally at least one oil and/or petroleum distillate and at least one surfactant. The surfactant is preferably a non-water soluble surfactant having an HLB number of less than about 6, and includes emulsifiers. A preferred surfactant is commercially sold as ATMOS® 300K, and is a combination of mono- and di-glycerides made from edible food sources and propylene glycol with an HLB of 2.8. Another preferred surfactant is Defospum E100, a defoamer which is a combination of mono- and di-glycerides sold by Defotec. A third preferred surfactant is Lucrafoam E100, a defoamer which is a combination of mono-, di- and tri-glycerides sold by Levaco Chemicals.

Certain surfactants are not compatible with the present invention, and cause the lotion to fail, in that the continuous phase oil enveloping the aqueous phase either doesn't form or quickly breaks down. For example, the Tween surfactants, having a hydrophilic ethylene glycol head and hydrophobic alkyl tail, cause the lotion to fail. Tween 20 is a polysorbate monooleate nonionic surfactant that causes the lotion to break down into separate phases.

The oil suitable for the oil phase is typically liquid or semi-solid at room temperature, and is compatible with the topical applications. Such oils include essential oils, plant oils, such as vegetable oil, corn oil, canola oil, coconut oil or olive oil, shea butter, and animal fats such as tallow and lard. The oils also include petroleum distillates, such as paraffin oil, petrolatum and mineral oil. Preferred oils include paraffin oil (low viscosity) and mineral oil. Mixtures of oils are also contemplated in the present invention. The oil phase is present in the lotion in the range of from about 5 to 20 wt. %. In a preferred embodiment, the surfactant and the oil are present in the lotion in a weight ratio of about 5:1 to 1:3 surfactant to oil.

Certain oils are not suitable for the present lotion. This includes castor oil, which contains triglycerides having about 90% fatty acid chains from ricinoleats. Oleates and linoleates are other significant components of castor oil.

Not all antiseptic agents are compatible with the present invention. Alcohols such as methanol, ethanol, propanol, isopropanol, and butanol will cause the lotion to fail. Preservative alcohols such as benzyl alcohol and phenoxyethanol cause the lotion to separate into phases and fail. However, sugar alcohols, such as fructose and sorbitol, will not adversely affect the lotion.

The aqueous phase contains at least one humectant. Suitable humectants include, but are not limited to glycerin, lactic acid, polyols, propylene glycol, corn syrup, high fructose corn syrup (HFCS), including Cornsweet 55 (55 wt. % fructose, 24 wt. % water and 21 wt. % glucose) and Cornsweet 42 (42 wt. % fructose, 24. wt. % water and 34 wt. % glucose), and sorbitol. The at least one humectant is present in the aqueous phase from 25 to 75 wt. %. Preferably, the amount of humectant in the lotion is from about 30 to 75 wt. %. More preferably, the humectant is present from about 40 to 70 wt. %.

A preferred humectant is glycerin, which works to stabilize the lotion. More preferably the humectants in the lotion are from about 15 to 40 wt. % glycerin, and from about 15 to 40 wt. % sorbitol solution. A preferred sorbitol solution is 70 wt. % non-crystalizing liquid sorbitol in water.

The antiseptic active of the present invention is formaldehyde which can be added as an aqueous solution, known as formalin (37 wt. % formaldehyde in water). Other sources of formaldehyde are also claimed in this invention. In a preferred embodiment, the formaldehyde is present in the lotion from about 2 to 10 wt. %. In a more preferred embodiment, the formaldehyde is present in the lotion from about 2 to 6 wt. %. If greater than about 12 wt. % formaldehyde is present in the invention, the lotion fails and separates.

The following Examples and Controls of the Antiseptic Lotion were made by the method below. All percents are by weight.

The claimed composition is typically prepared using a planetary or counter rotating type mixer having a rubber lined mixing bowl equipped with a wire whip stirring device. Preferably, the wire whip is rubber coated. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. The rubber coating of the wire whip device improves the rate of processing.

To prepare the Aqueous Phase, which contains formaldehyde, and at least one humectant, perform the following steps.

In suitable container, measure carefully and accurately, the Aqueous Phase ingredients. Set aside.

Prepare the Oil Phase which contains at least one oil and at least one oil soluble surfactant.

Carefully and accurately weigh the Oil Phase ingredients directly into a Hobart mixer bowl.

Place mixer bowl on stand mixer and start the Hobart mixer on the low speed setting.

Slowly begin adding the Aqueous Phase ingredients to the bowl with continuous mixing at low speed (setting 1). As the Antiseptic Lotion starts to form, add the Aqueous Phase faster until a slow pour is achieved. When 50% or more of the Aqueous Phase solution has been added, the Hobart mixer speed can be increased to no more than setting 2.

Continue adding until all of the Aqueous Phase solution is incorporated, taking care to scrape the bowl out, and making sure all of the solution is removed from the container.

Stop the mixer and scrape down the bowl and mixing blade.

Continuing mixing at setting 2 for an additional ten (10) minute.

Stop the mixer again and scrape down the bowl and mixing blade.

Mix for an additional five (5) minutes.

Remove from stand and scrape down the bowl and mixing blade. The antiseptic lotion is complete.

The components of the hydrophobic lotion have the following preferred wt. % ranges:

| Component | Wt. % |
| --- | --- |
| Surfactant: | 2.0-15.0 |
| Oil: | 2.0-15.0 |
| Humectant: | 25.0-75.0 |
| Water: | 10.0-50.0 |
| Formaldehyde: | 0.1-12.0 |

In a more preferred embodiment, the wt. % ranges for specific components are:

| ATMOS ®300 or Lucafoam | |
|---|---|
| Surfactant | 2.0-15.0 |
| Citation 70 mineral oil and/or paraffin oil | 2.0-15.0 |
| Glycerin | 15.0-40.0 |
| Sorbitol solution (70 wt. %) | 15.0-40.0 |
| Water | 10.0-50.0 |
| Formaldehyde | 2.0-10.0 |

In a second embodiment of the process of this invention, the lotion is prepared as a first step and a second step. The first step produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 12:1 to 1:2), this initial process step is concluded.

The second step begins with the seed batch of the first step, at the desired final weight ratio of aqueous phase to oil phase. The volume of seed material needed for the second step is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

Stability Testing

The lotion of the present invention is evaluated for stability by at least two (2) visual tests. In the first test, a small amount of lotion is spread in a thin layer on a microscope slide and observed periodically for about 24 hours. The layer is examined under a microscope at 10 to 40 times enlargement. It is examined for smoothness and glossiness, which indicates a successful formulation. If it is observed that the surface has cracking, pooling or pitting, then failure is determined. Also, signs of separating and the formation of two phases also indicates formulation failure.

For a second test, a cup is filled with deionized water and a portion of lotion is dropped into the water and submerges. The lotion is observed periodically for about 24 hour. A successful formulation for lotion expands (grows in size) due to absorbing water, intact, while submerged in the water. A failure includes lotion dissolving completely in the water, or floating on top of the water, or breaking into pieces which break when moved with spoonula.

Another test of the lotion is hand feel. The lotion should be non-greasy, non-drippy, yet smooth and silky feeling on the skin.

Another test of the lotion is the "sniff test", where it is determined if the odor of formaldehyde is present.

Example—1—4% Formaldehyde

| Ingredient | Weight | % |
|---|---|---|
| Oil Phase | | |
| ATMOS ®300 (surfactant) | 45.00 | 9.00% |
| Citation 70 (mineral oil) | 30.00 | 6.00% |
| Aqueous Phase | | |
| Formaldehyde 37% (active) | 54.00 | 10.80% (4.0% Formaldehyde, 6.8% water) |
| Sorbitol Solution 70% USP (humectant) | 185.50 | 37.10% (26.0% sorbitol, 11.1% water) |
| Glycerin, USP 99.7% Food use (humectant) | 185.50 | 37.10% |

Example—2—12% Formaldehyde

| Ingredient | Weight | % |
|---|---|---|
| ATMOS ®300 | 27.00 | 9.00% |
| Citation 70 | 18.00 | 6.00% |
| Aqueous Phase | | |
| Formaldehyde 37% | 97.20 | 32.40% (12.0% Formaldehyde, 20.4% water) |
| Sorbitol Solution 70% USP | 78.90 | 26.30% (18.4% sorbitol, 7.9% water) |
| Glycerin, USP 99.7% Excipient/Food use | 78.90 | 26.30% |

Control—3 No Humectant—12% Formaldehyde

| Ingredient | Weight | % |
|---|---|---|
| ATMOS ®300 | 27.00 | 9.00% |
| Citation 70 | 18.00 | 6.00% |
| Aqueous Phase | | |
| Formaldehyde 37% | 97.20 | 32.40% (12.0% Formaldehyde, 20.4% water) |
| purified water (Distilled) | 157.80 | 52.60% |

The above lotion prepared with no humectant was not stable and separated.

Example—4—12% Formaldehyde

| Ingredient | Weight | % |
|---|---|---|
| ATMOS ®300 | 36.00 | 12.00% |
| Citation 70 | 24.00 | 8.00% |

-continued

| Ingredient | Weight | % |
|---|---|---|
| Aqueous Phase | | |
| Formaldehyde 37% | 97.20 | 32.40% (12.0% Formaldehyde, 20.4% water) |
| Sorbitol Solution 70% USP | 71.40 | 23.80% (16.7% sorbitol, 7.1% water) |
| Glycerin, USP 99.7% Food use | 71.40 | 23.80% |

Control—5—16% Formaldehyde

| Ingredient | Weight | % |
|---|---|---|
| ATMOS ®300 | 27.00 | 9.00% |
| Citation 70 | 18.00 | 6.00% |
| Aqueous Phase | | |
| Formaldehyde 37% | 129.72 | 43.24% (16.0% Formaldehyde, 27.24% water) |
| Sorbitol Solution 70% USP | 62.64 | 20.9% (14.6% sorbitol, 6.3% water) |
| Glycerin, USP 99.7% Food use | 62.64 | 20.88% |

Having greater than about 12% formaldehyde causes the lotion to be unstable and separate.

Control—6—16% Formaldehyde-UV

Added to the formulation was 0.50 wt. % Keyfluor™ White OB by Millikenm which is a fluorescent blue white optical brightener. It is used in plastic applications as security taggants on manufactured goods, packaging, or within raw materials to validate product identification and authenticity. Keyfluor™ White OB is detected by ultraviolet light. It is used in the present invention to determine if the applied lotion adheres to and provides sustained antiseptic properties to the desired surface.

| Ingredient | Weight | % |
|---|---|---|
| ATMOS ®300 | 35.1000 | 11.70% |
| Citation 70 | 23.4000 | 7.80% |
| Keyfluor White OB (Fluorescent Brightener) | 1.5000 | 0.50% |
| Aqueous Phase | | |
| Formaldehyde (Formalin), 37% vvv | 129.7200 | 43.24% (16.0% Formaldehyde, 27.24% water) |
| Sorbitol Solution 70% USP | 55.1400 | 18.4% (12.9% sorbitol, 5.5% water) |
| Glycerin, USP 99.7% Excipient/Food use | 55.1400 | 18.38% |

Having greater than 12 wt. % Formaldehyde makes the lotion unstable.

Example—7—4% Formaldehyde-UV Detection

| Ingredient | Weight | % |
|---|---|---|
| ATMOS ®300 | 87.00 | 8.70% |
| Citation 70 | 58.00 | 5.80% |
| Keyfluor White OB | 5.00 | 0.50% |
| Aqueous Phase | | |
| Formaldehyde (Formalin), 37% vvv | 108.00 | 10.80% (4.0% Formaldehyde, 6.8% water) |
| Sorbitol Solution 70% USP | 371.00 | 37.10% (26.0% sorbitol, 11.1% water) |
| Glycerin, USP 99.7% Excipient/Food use | 371.00 | 37.10% |

Example—8—4% Formaldehyde-UV Detection

| Ingredient | Weight | % |
|---|---|---|
| ATMOS ®300 | 130.50 | 8.70% |
| Citation 70 | 87.00 | 5.80% |
| Keyfluor White OB | 7.50 | 0.50% |
| Aqueous Phase | | |
| Formaldehyde (Formalin), 37% vvv | 162.00 | 10.80% (4.0% Formaldehyde, 6.8% water) |
| Sorbitol Solution 70% USP | 556.50 | 37.10% (26.0% sorbitol, 11.1% water) |
| Glycerin, USP 99.7% Excipient/Food use | 556.50 | 37.10% |

Example—9—4% Formaldehyde-UV Detection

| Ingredient | Weight | % |
|---|---|---|
| ATMOS ®300 | 217.50 | 8.70% |
| Citation 70 | 145.00 | 5.80% |
| Keyfluor White OB | 12.50 | 0.50% |
| Aqueous Phase | | |
| Formaldehyde (Formalin), 37% | 270.00 | 10.80% (4.0% Formaldehyde, 6.8% water) |
| Sorbitol Solution 70% USP | 927.50 | 37.10% (26.0% sorbitol, 11.1% water) |
| Glycerin, USP 99.7% Excipient/Food use | 927.50 | 37.10% |

Example—10—12% Formaldehyde-UV Detection

| Ingredient | Weight | % |
|---|---|---|
| ATMOS ®300 | 217.50 | 8.70% |
| Citation 70 | 145.00 | 5.80% |
| Keyfluor White OB | 12.50 | 0.50% |
| Aqueous Phase | | |
| Formaldehyde (Formalin), 37% | 810.00 | 32.40% (12.0% Formaldehyde, 20.4% water) |

-continued

| Ingredient | Weight | % |
| --- | --- | --- |
| Sorbitol Solution 70% USP | 657.50 | 26.30%(18.4% sorbitol, 7.9% water) |
| Glycerin, USP 99.7% Excipient/Food use | 657.50 | 26.30% |

Example—11—12% Formaldehyde-UV Detection

| Ingredient | Weight | % |
| --- | --- | --- |
| ATMOS ®300 | 217.50 | 8.70% |
| Citation 70 | 145.00 | 5.80% |
| Keyfluor White OB | 12.50 | 0.50% |
| Aqueous Phase | | |
| Formaldehyde (Formalin), 37% | 810.00 | 32.40%(12.0% Formaldehyde, 20.4% water) |
| Sorbitol Solution 70% USP | 657.50 | 26.30%(18.4% sorbitol, 7.9% water) |
| Glycerin, USP 99.7% Excipient/Food use | 657.50 | 26.30% |

Example—12—4% Formaldehyde-UV Detection

| Ingredient | Weight | % |
| --- | --- | --- |
| ATMOS ®300 | 60.00 | 7.50% |
| Citation 70 | 20.00 | 2.50% |
| Keyfluor White OB | 4.00 | 0.50% |
| Aqueous Phase | | |
| Formaldehyde (Formalin), 37% | 86.40 | 10.80%(4.0% Formaldehyde, 6.8% water) |
| Sorbitol Solution 70% USP | 314.80 | 39.4%(27.6% sorbitol, 11.8% water) |
| Glycerin, USP 99.7% Excipient/Food use | 314.80 | 39.35% |

Example 13—4% Formaldehyde

| Ingredient | Weight | % |
| --- | --- | --- |
| ATMOS ®300 | 22.50 | 7.50% |
| Citation 70 | 7.50 | 2.50% |
| Aqueous Phase | | |
| Formaldehyde (Formalin), 37% | 32.40 | 10.80%(4.0% Formaldehyde, 6.8% water) |
| Sorbitol Solution 70% USP | 118.80 | 39.60%(27.7% sorbitol, 11.9% water) |
| Glycerin, USP 99.7% Excipient/Food use | 118.80 | 39.60% |

Example—14—4% Formaldehyde-LucraFoam Surfactant

| Ingredient | Weight | % |
| --- | --- | --- |
| Lucrafoam E100 Surfactant | 27.00 | 9.00% |
| Citation 70 mineral oil | 18.00 | 6.00% |
| Aqueous Phase | | |
| Formaldehyde 37% | 32.40 | 10.80%(4.0% Formaldehyde, 6.8% water) |
| Sorbitol Solution 70% USP | 111.30 | 37.10%(26.0% sorbitol, 11.1% water) |
| Glycerin, USP 99.7% Excipient/Food use | 111.30 | 37.10% |

This formulation was too thick. The amount of Lucrafoam surfactant was decreased and the amount of oil increased in Example—15, Example—16 and Example—17.

Example—15—4% Formaldehyde—LucraFoam Surfactant

| Ingredient | Weight | % |
| --- | --- | --- |
| LucraFoam E100 | 18.00 | 6.00% |
| Paraffin Oil Low Viscosity | 27.00 | 9.00% |
| Aqueous Phase | | |
| Formaldehyde (Formalin), 37% | 32.40 | 10.80%(4.0% Formaldehyde, 6.8% water) |
| Sorbitol Solution 70% USP | 111.30 | 37.10%(26.0% sorbitol, 11.1% water) |
| Glycerin, USP 99.7% Excipient/Food use | 111.30 | 37.10% |

Example—16—4.0% Formaldehyde, 4.5% LucraFoam Surfactant

| Ingredient | Weight | % |
| --- | --- | --- |
| LucraFoam E100 | 13.50 | 4.50% |
| Paraffin Oil Low Viscosity | 5.31 | 1.77% |
| Citation 70 | 26.19 | 8.73% |
| Aqueous Phase | | |
| Formaldehyde (Formalin), 37% | 32.40 | 10.80%(4.0% Formaldehyde, 6.8% water) |
| Sorbitol Solution 70% USP | 111.30 | 37.10%(26.0% sorbitol, 11.1% water) |
| Glycerin, USP 99.7% Excipient/Food use | 111.30 | 37.10% |

Example—17—4% Formaldehyde—Lucrafoam Surfactant

| Ingredient | Weight | % |
| --- | --- | --- |
| LucraFoam E100 | 18.00 | 6.00% |
| Citation 70 | 27.00 | 9.00% |

-continued

| Ingredient | Weight | % |
|---|---|---|
| Aqueous Phase | | |
| Formaldehyde (Formalin), 37% | 32.40 | 10.80% (4.0% Formaldehyde, 6.8% water) |
| Sorbitol Solution 70% USP | 111.30 | 37.10% (26.0% sorbitol, 11.1% water) |
| Glycerin, USP 99.7% Excipient/Food use | 111.30 | 37.10% |

Testing the Lotion—Bovine Hoof Treatment

Samples containing 12% formaldehyde with UV reflectant (Examples 10 and 11) and without UV reflectant (Examples 2 and 4) were tested using a walk-through hoof bath to apply the lotion to the hooves of cows. The 12% product was found to be too irritating and was discontinued. Samples containing 4% with UV reflectant (Examples 7, 8 9, and 12) and without UV reflectant (Examples 1, 13, 14, 15, 16 and 17) were tested in a walk-through hoof bath. Examination of the hooves using UV light indicated long term presence of the lotion which also indicated long term effectiveness of the treatment. The 4% lotion was non-irritating and effective in treating hoof disease. The lotion was free of the odor of formaldehyde.

The 4% lotion was also tested by painting the product on cow hooves, but proved more effective when used in a walk-through hoof bath.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An antiseptic topical lotion comprising:
at least one surfactant in the amount of 2.0-15.0 wt %;
at least one oil in the amount of 2.0-15.0 wt %;
at least one humectant in the amount of 25.0-75.0 wt %;
water in the amount of 10.0-50.0 wt %; and
formaldehyde in the amount of 2.0-10.0 wt %.

2. The lotion of claim 1, wherein the at least one surfactant is selected from the group consisting of monoglycerides, diglycerides, triglycerides and combinations thereof.

3. The lotion of claim 2, wherein the at least one surfactant further comprises a non-water soluble surfactant having an HLB number of less than about 6.

4. The lotion of claim 3, wherein the formaldehyde is in the amount of 4.0-10.0 Wt %.

5. The lotion of claim 1, wherein the formaldehyde is in the amount of 4 wt %.

6. A method for making an antiseptic topical lotion, wherein the method comprises combining:
at least one surfactant in the amount of 2.0-15.0 wt %;
at least one oil in the amount of 2.0-15.0 wt %;
at least one humectant in the amount of 25.0-75.0 wt %;
water in the amount of 10.0-50.0 wt %; and
formaldehyde in the amount of 2.0-10.0 wt %.

7. The method of claim 6, wherein the at least one surfactant is selected from the group consisting of monoglycerides, diglycerides, triglycerides, and combinations thereof.

8. The method of claim 7, wherein the formaldehyde is in the amount of 4.0-10.0 Wt %.

9. The method of claim 8, wherein the formaldehyde is in the amount of 6.0-10.0 Wt %.

10. The method of claim 7, wherein the formaldehyde is in the amount of 4 wt %.

* * * * *